United States Patent
Davila et al.

(10) Patent No.: US 12,005,103 B2
(45) Date of Patent: *Jun. 11, 2024

(54) UNIVERSAL ANTI-TAG CHIMERIC ANTIGEN RECEPTOR-EXPRESSING T CELLS AND METHODS OF TREATING CANCER

(71) Applicant: University of Maryland, Baltimore, Baltimore, MD (US)

(72) Inventors: Eduardo Davila, Cockeyville, MD (US); Koji Tamada, Ube (JP)

(73) Assignee: UNIVERSITY OF MARYLAND, Baltimore, MD (US)

( * ) Notice: Subject to any disclaimer, the term of this patent is extended or adjusted under 35 U.S.C. 154(b) by 299 days.

This patent is subject to a terminal disclaimer.

(21) Appl. No.: 17/228,001

(22) Filed: Apr. 12, 2021

(65) Prior Publication Data

US 2021/0330769 A1  Oct. 28, 2021

Related U.S. Application Data (63) Continuation of application No. 14/990,514, filed on Jan. 7, 2016, now Pat. No. 10,973,893, which is a continuation of application No. 13/993,396, filed as application No. PCT/US2011/064808 on Dec. 14, 2011, now Pat. No. 9,233,125.

(60) Provisional application No. 61/422,681, filed on Dec. 14, 2010.

(51) Int. Cl.
| | |
|---|---|
| A61K 39/00 | (2006.01) |
| A61K 35/17 | (2015.01) |
| A61K 39/395 | (2006.01) |
| A61K 47/54 | (2017.01) |
| A61K 47/68 | (2017.01) |
| C07K 16/28 | (2006.01) |
| C07K 16/44 | (2006.01) |
| C12N 5/0783 | (2010.01) |

(52) U.S. Cl.
CPC .......... *A61K 39/0011* (2013.01); *A61K 35/17* (2013.01); *A61K 39/39558* (2013.01); *A61K 47/555* (2017.08); *A61K 47/6855* (2017.08); *A61K 47/6859* (2017.08); *A61K 47/6863* (2017.08); *A61K 47/6897* (2017.08); *C07K 16/2863* (2013.01); *C07K 16/44* (2013.01); *C12N 5/0636* (2013.01); *A61K 2039/5156* (2013.01); *A61K 2039/572* (2013.01); *A61K 2039/585* (2013.01); *C07K 2317/622* (2013.01); *C07K 2319/00* (2013.01); *C12N 2501/515* (2013.01); *C12N 2510/00* (2013.01)

(58) Field of Classification Search
None
See application file for complete search history.

(56) References Cited

U.S. PATENT DOCUMENTS

| | | |
|---|---|---|
| 5,861,156 A | 1/1999 | George et al. |
| 5,906,936 A | 5/1999 | Eshhar et al. |
| 5,912,172 A | 6/1999 | Eshhar et al. |
| 9,233,125 B2 | 1/2016 | Davila |
| 10,973,893 B2 * | 4/2021 | Davila ............... A61K 47/6855 |
| 2003/0175288 A1 | 9/2003 | Itoh |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2006/0067920 A1 | 3/2006 | Jensen |
| 2007/0172504 A1 | 7/2007 | Shirwan et al. |
| 2009/0117108 A1 | 5/2009 | Wang et al. |
| 2010/0278830 A1 | 11/2010 | Shoemaker et al. |
| 2012/0034223 A1 | 2/2012 | Hall et al. |
| 2012/0213783 A1 | 8/2012 | Rosenberg et al. |

FOREIGN PATENT DOCUMENTS

| | | |
|---|---|---|
| JP | 2001-213804 | 8/2001 |
| JP | 2002-506046 | 2/2002 |
| WO | 99-45960 | 9/1999 |
| WO | 2010025177 | 3/2010 |
| WO | 2013/044225 | 3/2013 |

OTHER PUBLICATIONS

International Search Report and Written Opinion for PCT/US2011/064808 dated Jun. 21, 2012.
Sadelain, M. et al., The promise and potential pitfalls of chimeric antigen receptors. Curr. Opin. Immunol. 21, 215-223 (2009).
Gross, G. et al., Expression of immunoglobulin-T-cell receptor chimeric molecules as functional receptors with antibody-type specificity, Proc. Natl. Acad. Sci. U.S.A. 86, 10024-10028 (1989).
Ertl, H.C. et al., Considerations for the Clinical Application of Chimeric Antigen Receptor (CAR) T Cells: Observations from a Recombinant DNA Advisory Committee (RAC) Symposium Jun. 15, 2010, Cancer Res. 71(9), 3175-3181 (2011).
Kershaw, M.H. et al., A phase I study on adoptive immunotherapy using gene-modified T cells for ovarian cancer, Clin. Cancer Res. 12(20 Pt 1), 6106-6115 (2006).

(Continued)

*Primary Examiner* — Peter J Reddig
(74) *Attorney, Agent, or Firm* — Wenderoth, Lind & Ponack, L.L.P.

(57) ABSTRACT

The present invention provides a universal, yet adaptable, anti-tag chimeric antigen receptor (AT-CAR) system which provides T cells with the ability and specificity to recognize and kill target cells, such as tumor cells, that have been marked by tagged antibodies. As an example, αFITC-CAR-expressing T cells have been developed that specifically recognize various human cancer cells when those cells are bound by cancer-reactive FITC-labeled antibodies. The activation of αFITC-CAR-expressing T cells is shown to induce efficient target lysis, T cell proliferation, and cytokine/chemokine production. The system can be used to treating subjects having cancer.

18 Claims, 3 Drawing Sheets

Specification includes a Sequence Listing.

(56) References Cited

OTHER PUBLICATIONS

Lamers, C.H. et al., Treatment of metastatic renal cell carcinoma with autologous T-lymphocytes genetically retargeted against carbonic anhydrase IX: first clinical experience, J. Clin. Oncol. 24(13), e20-e22 (2006).
Morgan, R.A et al., Case report of a serious adverse event following the administration of T cells transduced with a chimeric antigen receptor recognizing ERBB2, Mol. Ther. 18(4), 843-851 (2010).
Pule, M.A. et al., Virus-specific T cells engineered to coexpress tumor-specific receptors: persistence and antitumor activity in individuals with neuroblastoma, Nat. Med. 14(11), 1264-1270 (2008).
Till, B.G. et al., Adoptive immunotherapy for indolent non-Hodgkin lymphoma and mantle cell lymphoma using genetically modified autologous CD20-specific T cells, Blood 112(6), 2261-2271 (2008).
Brentjens, R.J. et al., Eradication of systemic B-cell tumors by genetically targeted human T lymphocytes co-stimulated by CD80 and interleukin-15, Nat. Med. 9(3), 279-286 (2003).
Johnson, L.A. et al., Gene therapy with human and mouse T-cell receptors mediates cancer regression and targets normal tissues expressing cognate antigen, Blood 114(3), 535-546 (2009).
Yamada, K. et al., Development of the novel magnetite exhibiting dendric accumulation onto cancer cell surface for active hyperthemia treatment, Proceedings of the Chemical Society of Japan Meeting, 2008, 88(1):613, 2PA-055.
Friedmann-Morvinski, D. et al., Redirected primary T cells harboring a chimeric receptor require costimulation for their antigen-specific activation, Blood 105(8), 3087-3093 (2005).
Gillies, S.D. et al., Targeting Human Cytotoxic T Lymphocytes to Kill Heterologous Epidermal Growth Factor Receptor-Bearing Tumor Cells, The Journal of Immunology 146(3), 1067-1071 (1991).
Hwu, P. et al., Lysis of Ovarian Cancer Cells by Human Lymphocytes Redirected with a Chimeric Gene Composed of an Antibody Variable Region and the Fc Receptor gamma-Chain, The Journal of Experimental Medicine 178, 361-366 (1993).
Kershaw, M.H. et al., Gene-Engineered T Cells as a Superior Adjuvant Therapy for Metastatic Cancer, The Journal of Immunology 173(3) 2143-2150 (2004).
Lobbestael, E. et al., Immunohistochemical detection of transgene expression in the brain using small epitope tags, BMC Biotechnology 10:16 (2010).
Ma, Q. et al., Carcinoembryonic antigen-immunoglobulin Fc fusion protein (CEA-Fc) for identification and activation of anti-CEA immunoglobulin-T-cell receptor-modified T cells, representative of a new class of Ig fusion proteins, Cancer Gene Therapy 11, 297-306 (2004).
Oshimi, K. et al., Increased Lysis of Patient CD10-Positive Leukemic Cells by T Cells Coated With Anti-CD3 Fab' Antibody Cross-Linked to Anti-CD10 Fab' Antibody, Blood 77(5), 1044-1049 (1991).
Shirasu, N. et al., Construction and Molecular Characterization of Human Chimeric T-Cell Antigen Receptors Specific for Carcinoembryonic Antigen, Anticancer Research 30, 2731-2738 (2010).
Xiang, J. et al., Production of hybrid bispecific antibody recognizing human colorectal carcinoma and CD3 antigen, Mol. Biother. 4, 15-23 (1992).
Abcam Product Datasheet, accessed Jan. 23, 2015, 4 pages.
Fernando et al., The Oncologist 2004; 9(suppl. 1): 11-18.
Arcondeguy et al., Nucl. Acids Res. 2013; 41(17): 7997-8010.
Extended European Search Report dated May 2, 2016 in corresponding European Application No. 11849221.4.
Zhong et al., "Chimeric Antigen Receptors Combining 4-1BB and CD28 Signaling Domains Augment Pl3kinase/AKT /Bcl-$X_L$ Activation and CD8+ T Cell-mediated Tumor Eradication", Molecular Therapy, Feb. 2010, vol. 18, No. 2, pp. 413-420.
Patel et al., "T-cell killing of heterogenous tumor or viral targets with bispecific chimeric immune receptors", Cancer Gene Therapy, 2000, vol. 7, No. 8., pp. 1127-1134.

Zhao et al., "A Herceptin-Based Chimeric Antigen Receptor with Modified Signaling Domains Leads to Enhanced Survival of Transduced Lymphocytes and Antitumor Activity", The Journal of Immunology, 2009, vol. 183, pp. 5563-5574.
Urbanska et al., "A Universal Strategy for Adoptive Immunotherapy of Cancer through Use of a Novel T-cell Antigen Receptor", Cancer Research, vol. 72, No. 7, Apr. 1, 2012, pp. 1844-1852.
Rodgers et al., "Switch-mediated activation and retargeting of CAR-T cells for B-cell malignancies", PNAS, Jan. 26, 2016, vol. 113, No. 4, pp. E459-E468.
Wu et al., "Remote control of therapeutic T cells through a small molecule-gated chimeric receptor", Science, Oct. 16, 2015, vol. 350, Issue 6258, p. 293 and aab4077-1 through aab4077-10.
Frost et al. (Cancer Feb. 15, 2010 116(4 suppl.): 1101-10).
Ang et al. (Molecular Therapy May 2011 19 (S1): S137-S138, Ab. No. 353) (Year: 2011).
Urbanska et al. (J. Immunotherapy Nov. 011 34(9): 681) (Year: 2011).
Rueckert et al. (Expert Opinion Biol. Ther. 2005 5(6): 853-856) (Year: 2005).
Jena et al. (Blood Aug. 19, 2010, 116(7) : 1035-1044), (Year: 2010).
Declaration of Roderick O'Connor, Ph.D., filed with petition for Inter Partes Review of U.S. Pat. No. 9,233,125, Dec. 20, 2019.
Ang et al., "Generating a Chimeric Antigen Receptor To Redirect T-Cell Specificity after Infusion," Molecular Therapy, May 2011, vol. 19, Supplement 1, pp. S137-S138 and i-xv.
Tan et al., "A Nanoengineering Approach for Investigation and Regulation of Protein Immobilization," ACS NANO, Oct. 29, 2008, vol. 2, No. 11, pp. 2374-2384.
Javier et al., "Aptamer-Targeted Gold Nanoparticles As Molecular-Specific Contrast Agents for Reflectance Imaging," Bioconjugate Chem, May 31, 2008, vol. 19, No. 6, pp. 1309-1312.
Andersen et al., "Cytotoxic T Cells," Journal of Investigative Dermatology, Jan. 2006, vol. 126, pp. 32-41.
Gerber, D.E., "Targeted Therapies: A New Generation of Cancer Treatments," American Family Physician, Feb. 1, 2008, vol. 77, No. 3, pp. 311-319.
Sharkey et al., "Targeted Therapy of Cancer: New Prospects for Antibodies and Immunoconjugates," A Cancer Journal for Clinicians, Jul. 2006, vol. 56, No. 4, pp. 226-243.
Adams et al., "Monoclonal antibody therapy of cancer," Nature Biotechnology, Sep. 2005, vol. 23, No. 9, pp. 1147-1157.
Murphy et al., "Chapter 3: Antigen Recognition by B-cell and T-cell Receptors," Janeway's Immunobiology (7th Edition), Garland Science Taylor & Francis Group, 2008, pp. 111-142.
Macrea, E.R., "Immunohistochemistry: Roots and Review," Laboratory Medicine, Dec. 1999, vol. 30, No. 12, pp. 787-790.
Childs, G.V., "Immunohistochemistry: History of Immunohistochemistry," Elsevier, 2014, pp. 3775-3796.
Scott et al., "Monoclonal antibodies in cancer therapy," Cancer Immunity, May 1, 2012, vol. 12, pp. 1-8.
Kulemzin et al., "Engineering Chimeric Antigen Receptors," ACTA Naturae, 2017, vol. 9, No. 1, pp. 6-14.
Murphy et al., "Chapter 9: The Humoral Immune Response," Janeway's Immunobiology (7th Edition), Garland Science Taylor & Francis Group, 2008, pp. 379-420.
Nelson, A.L., "Antibody fragments: Hope and hype," Landes Bioscience, Jan. 2010, vol. 2. Issue 1, pp. 77-83.
Attarwala, H., "Role of antibodies in cancer targeting," Journal of Natural Science, Biology and Medicine, Jul. 2010, vol. 1, Issue 1, pp. 53-56.
Carter et al., "Identification and validation of cell surface antigens for antibody targeting in oncology," Endocrine-Related Cancer, 2004, vol. 11, pp. 659-687.
Schrama et al., "Antibody targeted drugs as cancer therapeutics," Nature Reviews Drug Discovery, Feb. 2006, vol. 5, pp. 147-159.
Reichert, J.M., "Antibody-based therapeutics to watch in 2011," Landes Bioscience, Jan. 2011, vol. 3, Issue 1, pp. 76-99.
Wu et al., "Antibodies for Molecular Imaging of Cancer," The Cancer Journal, May 2008, vol. 14, No. 3, pp. 191-197.
Koivunen et al., "Principles of Immunochemical Techniques Used in Clinical Laboratories," Lab Medicine, Aug. 2006, vol. 37, No. 8, pp. 490-497.

(56) References Cited

OTHER PUBLICATIONS

Duraiyan et al., "Applications of immunohistochemistry," Journal of Pharmacy and Bioallied Sciences, Aug. 2012, vol. 4, pp. S307-S309.
Leach et al., "Use of Tissue Cross-reactivity Studies in the Development of Antibody-based Biopharmaceuticals: History, Experience, Methodology, and Future Directions," Toxicologic Pathology, 2010, vol. 38, No. 7, pp. 1138-1166.
Haugland et al., "Coupling of Antibodies with Biotin," The Protein Protocols Handbook (2nd Edition), Humana Press Inc., 2002, pp. 355-363.
Murphy et al., "Chapter 8: T Cell-Mediated Immunity," Janeway's Immunobiology (7th Edition), Garland Science Taylor & Francis Group, 2008, pp. 323-377.
Murphy et al., "Chapter 4: The Generation of Lymphocyte Antigen Receptors," Janeway's Immunobiology (7th Edition), Garland Science Taylor & Francis Group, 2008, pp. 143-179.
Smith-Garvin et al., "T Cell Activation," Annual Review of Immunology, 2009, vol. 27, pp. 591-619.
Cartellieri et al., "Chimeric Antigen Receptor-Engineered T Cells for Immunotherapy of Cancer," Journal of Biomedicine and Biotechnology, 2010, vol. 2010, pp. 1-13.
Rosenberg et al., "Adoptive cell transfer: a clinical path to effective cancer immunotherapy," Nature Reviews Cancer, Apr. 2008, vol. 8, pp. 299-308.
Kohler et al., "Matched Sizes of Activating and Inhibitory Receptor/Ligand Pairs Are Required for Optimal Signal Integration by Human Natural Killer Cells," PLoS One, Nov. 2010, vol. 5, Issue 11, pp. 1-11.
Choudhuri et al., "T-cell receptor triggering is critically dependent on the dimensions of its peptide-MHC ligand," Nature Publishing Group, Jul. 2005, vol. 436, pp. 578-582.
Kunkele et al., "Functional Tuning of CARs Reveals Signaling Threshold above Which CD8+ CTL Antitumor Potency Is Attenuated due to Cell Fas-FasL-Dependent AICD," Cancer Immunology Research, Apr. 2015, vol. 3, Issue 4, pp. 368-379.
Hudecek et al., "The Nonsignaling Extracellular Spacer Domain of Chimeric Antigen Receptors Is Decisive for In Vivo Antitumor Activity," Cancer Immunology Research, Feb. 2015, vol. 3, Issue 2, pp. 125-135.
James et al., "Antigen Sensitivity of CD22-Specific Chimeric TCR Is Modulated by Target Epitope Distance from the Cell Membrane," The Journal of Immunology, 2008, vol. 180, Issue 10, pp. 7028-7038.
Singh et al., "Single Chain Variable Fragment Linker Length Regulates CAR Biology and T Cell Efficacy," The American Society of Hematology, Nov. 2019, vol. 134, pp. 1-5.
Hirsch et al., "Easily reversible desthiobiotin binding to streptavidin, avidin, and other biotin-binding proteins: uses for protein labeling, detection, and isolation," Analytical Biochemistry, 2002, vol. 308, pp. 343-357.
Kay et al., "High-Throughput Biotinylation of Proteins," Methods in Molecular Biology: High Throughput Protein Expression and Purification, 2009, vol. 198, pp. 185-198.
Diamandis et al., "The Biotin-(Strept)Avidin System: Principles and Applications in Biotechnology," Clinical Chemistry, 1991, vol. 37, No. 5, pp. 625-636.
Zempleni et al., "Biotin," BioFactors, Jan. 2009, vol. 35, No. 1, pp. 36-46.
Boenisch et al., Handbook Immunochemical Staining Methods (3rd Edition), DAKO Corporation, 2001, pp. 5-68.
Zhao et al., "Multiple Injections of Electroporated Autologous T Cells Expressing a Chimeric Antigen Receptor Mediate Regression of Human Disseminated Tumor," Cancer Research, vol. 70, Issue 22, pp. 9053-9061.
Chinnasamy et al., "Gene therapy using genetically modified lymphocytes targeting VEGFR-2 inhibits the growth of vascularized syngenic tumors in mice," The Journal of Clinical Investigation, Nov. 2010, vol. 120, No. 11, pp. 3953-3968.
Zabriskie et al., Essential Clinical Immunology, Cambridge University Press, 2009, pp. 1-362.
Fitzer-Attas et al., "Harnessing Syk Family Tyrosine Kinases as Signaling Domains for Chimeric Single Chain of the Variable Domain Receptors: Optimal Design for T Cell Activation," The Journal of Immunology, 1998, vol. 160, pp. 145-154.
Yan et al., "HLA-A Gene Polymorphism Defined by High-Resolution Sequence-Based Typing in 161 Northern Chiense Han People," Geno., Prot. & Bioinfo, Nov. 2003, vol. 1, No. 4, pp. 304-309.
Craddock et al., "Adoptive cellular therapy with T cells specific for EBV-derived tumor antigens," Update On Cancer Therapeutics, 2008, vol. 3, pp. 33-41.
Ang et al., "Generating a Chimeric Antigen Receptor To Redirect T-Cell Specificity after Infusion," Molecular Therapy Methods & Clinical Development, May 2011, vol. 19, pp. 1-3.
Petition For Inter Partes Review of U.S. Pat. No. 9,233,125, Dec. 20, 2019.

\* cited by examiner

FIG. 3

SEQUENCE LISTING

```
<160> NUMBER OF SEQ ID NOS: 1

<210> SEQ ID NO 1
<211> LENGTH: 815
<212> TYPE: DNA
<213> ORGANISM: Artificial Sequence
<220> FEATURE:
<223> OTHER INFORMATION: chemically synthesized anti-FITC-CAR sequence

<400> SEQUENCE: 1
agttgcctgt taggttgttg gtgctgatgt tctggattcc tgcttccagc agtgatgtcg      60
tgatgaccca aactccactc tccctgcctg tcagtcttgg agatcaagcc tccatctctt     120
gcagatctag tcagagcctt gtacacagta atggaaacac ctatttacgt tggtacctgc     180
agaagccagg ccagtctcca aaggtcctga tctacaaagt ttccaaccga ttttctgggg     240
tcccagacag gttcagtggc agtggatcag ggacagattt cacactcaag atcagcagag     300
tggaggctga ggatctggga gtttatttct gctctcaaag tacacatgtt ccgtggacgt     360
tcggtggagg caccaagctg gaaatcaaaa gtagtgctga tgatgctaag aaggatgctg     420
ctaagaagga tgatgctaag aaggatgatg ctaagaagga tggtgaggtg aagctggatg     480
agactggagg aggcttggtg caacctggga ggcccatgaa actctcctgt gttgcctctg     540
gattcacttt tagtgactac tggatgaact gggtccgcca gtctccagag aaaggactgg     600
agtgggtagc acaaattaga aacaaacctt ataattatga aacatattat tcagattctg     660
tgaaaggcag attcaccatc tcaagagatg attccaaaag tagtgtctac ctgcaaatga     720
acaacttaag agttgaagac atgggtatct attactgtac gggttcttac tatggtatgg     780
actactgggg tcaaggaacc tcagtcaccg tctcc                                815
```

UNIVERSAL ANTI-TAG CHIMERIC ANTIGEN RECEPTOR-EXPRESSING T CELLS AND METHODS OF TREATING CANCER

STATEMENT OF FEDERALLY SPONSORED RESEARCH AND DEVELOPMENT

This invention was made with government support under Grant Numbers CA140917 and HL088954 awarded by the National Institutes of Health. The government has certain rights in the invention.

SEQUENCE LISTING

A sequence listing in electronic (ASCII text file) format is filed with this application and incorporated herein by reference. The name of the ASCII text file is "Sequence Listing ST25.txt"; the file was created on Apr. 9, 2021; the size of the file is 1,545 bytes.

TECHNICAL FIELD

The invention relates to T cell-based anti-cancer therapeutics and methods of using the therapeutics in the treatment of cancer.

BACKGROUND OF INVENTION

The ability to make a universal yet versatile system to generate T cells that are capable of recognizing various types of cancers has important clinical implications for the use of T cell-based therapies. One current strategy incorporates the use of genetic engineering to express a chimeric antigen receptor (CAR) on T cells. The extracellular domain of a typical CAR consists of the $V_H$ and $V_L$ domains—single-chain fragment variable (scFv)—from the antigen binding sites of a monoclonal antibody. The scFv is linked to a flexible transmembrane domain followed by a tyrosine-based activation motif such as that from CD3ζ (Sadelain et al. *Curr. Opin. Immunol.* 21, 215-223 (2009); Gross et al. *Proc. Natl. Acad. Sci. USA* 86, 10024-10028 (1989); Ertl et al. *Cancer Res.* 71, 3175-3181 (2011). The so-called second and third generation CARs include additional activation domains from co-stimulatory molecules such as CD28 and CD137 (41BB) which serve to enhance T cell survival and proliferation. CAR T cells offer the opportunity to seek out and destroy cancer cells by recognizing tumor-associated antigens (TAA) expressed on their surface (Sadelain et al. *Curr. Opin. Immunol.* 21, 215-223 (2009)). As such, the recognition of a tumor cells occurs via an WIC-independent mechanism. Various preclinical and early-phase clinical trials highlight the efficacy of CAR T cells to treat cancer patients with solid tumors and hematopoietic malignancies (Kershaw et al. *Clin. Cancer Res.* 12, 6106-6115 (2006); Lamers et al. *J. Clin. Oncol.* 24, e20-e22 (2006); Morgan et al. *Mol. Ther.* 18, 843-851 (2010); Pule et al. *Nat. Med.* 14, 1264-1270 (2008); Till et al. *Blood* 112, 2261-2271 (2008)).

Despite of the promise that CAR T cells might have in treating cancer patients there are several limitations to the generalized clinical application of CAR T cells. First, since no single tumor antigen is universally expressed by all cancer types, scFv in CAR needs to be constructed for each tumor antigen to be targeted. Second, the financial cost and labor-intensive tasks associated with identifying and engineering scFvs against a variety of tumor antigens poses a major challenge. Third, tumor antigens targeted by CAR could be down-regulated or mutated in response to treatment resulting in tumor evasion. Since current CAR T cells recognize only one target antigen, such changes in tumors negate the therapeutic effects. Therefore, the generation of CART cells capable of recognizing multiple tumor antigens is highly desired. Finally, CAR T cells react with target antigen weakly expressed on non-tumor cells, potentially causing severe adverse effects (Morgan et al. *Mol. Ther.* 18, 843-851 (2010)). To avoid such "on-target off-tumor" reaction, use of scFvs with higher specificity to tumor antigen is required. And although ongoing studies are focused on generating methods to shut off CAR T cells in vivo this system has yet to be developed and might pose additional inherent challenges.

Modifications to existing CAR T cell systems that address and overcome the hurdles currently preventing development of the systems into effective means of in vivo treatment are therefore needed.

BRIEF SUMMARY OF INVENTION

The present invention provides a universal, yet adaptable, anti-tag chimeric antigen receptor (AT-CAR)-expressing T cell system that fully addresses the deficiencies of current systems. The system uses a gene therapy platform to generate immune cells capable of recognizing various cancers types and that have broad and valuable clinical implications for the use of T cell-based therapies. As disclosed herein, a versatile AT-CAR system which grants T cells specificity to recognize and bind tagged proteins, such as antibodies, has been developed.

For example, and as further described herein, αFITC-CAR-expressing human T cells have been developed that specifically recognize various human cancer cells when those cells are bound by cancer-reactive FITC-labeled antibodies. The activation of αFITC-CAR-expressing T cells is shown to induce efficient target lysis, T cell proliferation, and cytokine/chemokine production in vitro and ex vivo. In vivo, αFITC-CAR-expressing T cells plus FITC-cetuximab (Ctx) are shown to delay colon cancer tumor establishment but lead to the selection of tumor-associated antigen (TAA)—negative cancer cells. Using a pancreatic tumor model with uniform TAA expression, αFITC-CAR-expressing T cells were observed to eradicate an established tumor and prevent tumor growth. This 'off'-the-shelf system advances existing CAR technology through its potential to target various tagged proteins in the treatment of cancer patients.

In certain embodiments, the invention is drawn to a method of treating cancer in a subject, comprising: (a) administering a formulation of tagged proteins to a subject in need of treatment, wherein the tagged proteins bind a cancer cell in the subject, and (b) administering a therapeutically-effective population of anti-tag chimeric antigen receptor (AT-CAR)-expressing T cells to the subject, wherein the AT-CAR-expressing T cells bind the tagged proteins and induce cancer cell death, thereby treating cancer in a subject.

In a related embodiment, the invention is drawn to a method of treating cancer in a subject, comprising: (a) administering one or more formulations of tagged proteins to a subject in need of treatment, wherein the tagged proteins bind a cancer cell in the subject, and (b) administering one or more therapeutically-effective populations of AT-CAR-expressing T cells to the subject, wherein the AT-CAR-expressing T cells bind the tagged proteins and induce cancer cell death, thereby treating cancer in a subject.

In a further related embodiment, the invention is drawn to a method of treating cancer in a subject, comprising: (a) administering at least two formulations of tagged proteins to a subject in need of treatment, wherein the tagged proteins bind a cancer cell in the subject, and (b) administering at least two therapeutically-effective populations of AT-CAR-expressing T cells to the subject, wherein the AT-CAR-expressing T cells bind the tagged proteins and induce cancer cell death, thereby treating cancer in a subject.

In particular aspects of the embodiments of the invention, the tag of each formulation of tagged proteins is the same or different and the tag is selected from the group consisting of fluorescein isothiocyanate (FITC), streptavidin, biotin, histidine, dinitrophenol, peridinin chlorophyll protein complex, green fluorescent protein, phycoerythrin (PE), horse radish peroxidase, palmitoylation, nitrosylation, alkalanine phosphatase, glucose oxidase, and maltose binding protein.

In particular aspects of the embodiments of the invention, the protein of each formulation of tagged proteins is the same or different and the protein is an antibody or an antigen-binding fragment thereof. In preferred aspects, the antibody or antigen-binding fragment thereof is cetuximab, nimotuzumab, panitumumab, retuximab, omalizumab, tositumomab, trastuzumab, gemtuzumab, alemtuzumab, bevacizumab or an antigen-binding fragment of any one thereof.

In particular aspects of the embodiments of the invention, the AT-CAR of each population of AT-CAR-expressing T cells is the same or different and the AT-CAR comprises a tag-binding domain, a transmembrane domain, and an activation domain. In preferred aspects, the tag-binding domain is an antibody or an antigen-binding fragment thereof. In preferred aspects, the tag-binding domain specifically binds FITC, biotin, PE, histidine or streptavidin. In preferred aspects where the tag-binding domain is antigen-binding fragment, the antigen-binding fragment is a single chain variable fragment (scFv), such as a scFv that specifically binds FITC, biotin, PE, histidine or streptavidin. In preferred aspects the transmembrane domain is the hinge and transmembrane regions of the human CD8α chain. In preferred aspects, the activation domain comprises one or more of the cytoplasmic region of CD28, the cytoplasmic region of CD137 (41BB), OX40, HVEM, CD3ζ and FcRε.

In particular aspects of the embodiments of the invention, the T cells of each population of AT-CAR-expressing T cells are the same or different and wherein the T cells are selected from the group consisting of T cells of any HLA-background from peripheral blood mononuclear cells (PBMC), T cells isolated from a tumor explant of the subject, and intratumoral T cells of the subject.

In particular aspects of the embodiments of the invention, the T cells of each population of AT-CAR-expressing T cells consist of HLA-A2+ peripheral blood mononuclear cells (PBMC).

In particular aspects of the embodiments of the invention, the formulation(s) of tagged proteins are administered to the subject prior to administration of the therapeutically-effective population(s) of AT-CAR-expressing T cells.

In particular aspects of the embodiments of the invention, the formulation(s) of tagged proteins are administered to the subject concurrently with administration of the therapeutically-effective population(s) of AT-CAR-expressing T cells.

In particular aspects of the embodiments of the invention, the formulation(s) of tagged proteins are administered to the subject after administration of the therapeutically-effective population(s) of AT-CAR-expressing T cells.

In particular aspects of the embodiments of the invention, the formulation(s) of tagged proteins and the therapeutically-effective population(s) of AT-CAR-expressing T cells are administered to the subject in any order.

In particular aspects of the embodiments of the invention, AT-CAR-expressing T cell binding to the tagged proteins induces cytolytic activation of the T cells.

In particular aspects of the embodiments of the invention, the subject is a human.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other formulations for carrying out the same purposes of the present invention. It should also be realized by those skilled in the art that such equivalent formulations do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1. Anti-FITC-CAR expression, characterization and in vitro functionality. (A) Diagram of the anti-FITC-CAR (αFITC-CAR). Boxed diagram on left shows the genetic elements included in the polynucleotide engineered to express αFITC-CAR, beginning with a 5'-long terminal repeat, and followed by the coding region for anti-FITC scFv, CD28 transmembrane domain, CD28, 41BB, zeta chain (ζ) and a 3'-long terminal repeat. Figure on right shows the αFITC-CAR polypeptide traversing the T cell membrane and position to bind a tumor-reactive antibody labeled with FITC. (B) HLA-A2$^+$ PBMCs were activated with anti-CD3 antibodies in the presence of IL-2 followed by transduction with αFITC-CAR retrovirus. αFITC-CAR expression was determined by staining cells with CD3 and FITC-conjugated cetuximab (FITC-Ctx) or FITC-conjugated dextran beads (FITC-Dex). Cetuximab is an antibody with binding specificity for EGFR-expressing tumor cells. (C) αFITC-CAR functionality on transduced and control T cells was examined in proliferation assays using plate-bound FITC-Ctx, FITC-Dex or Ctx. (D) The proliferation of αFITC-CAR T cells and control T cells was measured in response to stimulation with SW480 colon cancer cells stained with titrating concentrations of FITC-Ctx. (E) T cell cytotoxicity by αFITC-CAR and control T cells was measured against SW480 colon cancer cells stained with FITC-Ctx or FITC-mouse IgG. (F) αFITC-CAR cytotoxicity was measured against Panc 6.03 stained with unlabeled Ctx and Her2 antibodies or stained with FITC-Ctx or FITC-Her2 at various effector to target ratios. Alternatively AU565 breast cancer cells were stained with FITC-Her2 or unlabeled Her2 mAb. All data are representative of three or more independent experiments each yielding identical trends.

FIG. 2. αFITC-CAR T cells delay tumor establishment but promote the growth of antigen-negative tumor cells. (A) SW480 human colon cancer cells were injected subcutaneously into NSG mice followed by injection with FITC-Ctx (i.p.) one day later. Twenty four hours after, $5 \times 10^6$ αFITC-CAR T cells were injected into the tail vein. FITC-Ctx was injected (i.p.) weekly for three weeks. Data are representative of two or three experiments (three or more mice per group). *, P≤0.02, ANOVA; n.s. not significant. (B) The percentage of $CD3^+$ αFITC-CAR positive and negative T cells was determined by flow cytometry. The average percentage of αFITC-CAR$^+$ T cells prior to injection or from the tumor explant of four mice is shown. (C) Tumor explants were finely minced and cultured in trypsin for 2 hours at 37° C. followed by T cell enrichment using a negative selection kit. T cells were co-cultured with SW480 colon cancer cells which had been pulsed with FITC-Ctx or Ctx ($0.5 \mu g/1 \times 10^6$ cells). Three days later proliferation was determined by [$^3$H]thymidine uptake (±SD). (D) Alternatively, cytokine and chemokine production was measured using a Milliplex array 72 hours after stimulation. (E) EGFR expression on SW480 tumor explants or SW480 cells taken from tissue culture was examined by flow cytometry using FITC-Ctx.

FIG. 3. αFITC-CAR T cells prevent tumor growth and eradicate established tumors. (A) EGFR expression on the pancreatic human cancer cells (Panc 6.03) was determined by staining cells with FITC-Ctx or with control antibody FITC-mIgG and analyzed by flow cytometry. (B) In the prophylactic tumor model, Panc 6.03 cells were injected subcutaneously into NSG mice (n=5) followed by injection with FITC-Ctx (i.p.) one day later. Twenty four hours later $5 \times 10^6$ αFITC-CAR T cells were injected into the tail vein. 25 µg of FITC-Ctx or Ctx was injected (i.p.) weekly for three weeks. Tumor growth and mouse survival is shown. (C) In the therapeutic model Panc 6.03 tumors were grown to sizes between 3-10 mm$^2$ and then injected (i.p.) with 25 µg of FITC-Ctx or Ctx every week for three weeks. One day after the first injection of FITC-Ctx, mice were administered $5 \times 10^6$ αFITC-CAR T cells via tail vein injection. *, P<0.02, ANOVA; n.s. not significant.

DETAILED DESCRIPTION OF THE INVENTION

I. Definitions

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

An adaptable generation of CARs has been developed which allows for the widespread use of personalized T cell-based immunotherapy. Human T cells have been engineered to express an anti-FITC CAR-CD28-41BB-CD3ζ (referred to αFITC-CAR). This platform takes advantage of the high affinity interaction between the anti-FITC scFv (on the cell's surface) and FITC as well as the ability to cheaply and easily conjugated FITC molecules (or other tags) to any anti-cancer-based monoclonal antibody such as cetuximab (anti-EGFR), retuximab (anti-CD20) and herceptin (anti-Her2) used to treat patients with various types of cancers. This system allows for extreme specificity to the antigen and is accompanied by robust effector function and proliferative capacity with no cross-reactivity to 'self-antigens'.

Effector cells. The effector cells used in the methods of the present invention may be autologous, syngeneic or allogeneic, with the selection dependent on the disease to be treated and the means available to do so. Suitable populations of effector cells that may be used in the methods include any immune cells with cytolytic activity, such as T cells, cytokine induced killer (CIK) cells, natural killer (NK) cells, tumor infiltrating lymphocytes (TILs), macrophages and microglia. Exemplary sub-populations of T cells include, but are not limited to those expressing $CD3^+$ including $CD3^+CD8^+$ T cells, $CD3^+CD4^+$ T cells, gamma delta T cells and natural killer T (NKT) cells. In one aspect, the T cells are HLA-A2+ peripheral blood mononuclear cells (PBMC) but the T cells can be of any HLA background from PBMCs and utilized in an autologous, syngeneic or allogeneic system. T cells may also be isolated from any source, including from a tumor explant of the subject being treated or intratumoral T cells of the subject being treated. For the sake of convenience, the effector cells are commonly referred to herein as T cells, but it should be understood that any reference to T cells, unless otherwise indicated, is a reference to all effector cell types as defined herein.

Anti-tag chimeric antigen receptor (AT-CAR). The skilled artisan will appreciate that the anti-tag chimeric antigen receptor (AT-CAR) expressed by the T cells used in the methods of the present invention allow for great flexibility. The sole requirements for the AT-CARs used in the methods are (i) that the AT-CAR has binding specificity for a particular tag that can be conjugated to a protein (such as an antibody) that binds to a tumor-associated antigen (TAA), and (ii) that T cells can be engineered to express the AT-CAR. Additional features that are preferred, but not required, include (i) that the AT-CAR includes an activation domain that induces efficient target lysis upon T cell binding and activation, and (ii) the ability to replace the scFv portion of the AT-CAR with one of specificity to other tags, such as biotin or phycoerythrin, which can be conjugated to target (i.e., tumor)-reactive proteins such as antibodies to be used in vivo.

In particular aspects, the AT-CAR comprises three domains. The first domain is the tag-binding domain. This domain is typically present at the amino terminal end of the polypeptide that comprises the AT-CAR. Locating the tag-binding domain at the amino terminus permits the tag-binding domain unfettered access to the tagged protein that is bound to the target cell. As used herein, the tag-binding domain is typically an antibody or an antigen-binding fragment thereof. The identity of the antibody or fragment is only limited by the identity of the tag of the tagged protein. For example, the antibodies may be obtained from any species of animal, though preferably from a mammal such as a human, simian, mouse, rat, rabbit, guinea pig, horse, cow, sheep, goat, pig, dog or cat. Preferably the antibodies are human or humanized antibodies. Nor is there a limitation on the particular class of antibody that may be used, including IgG1, IgG2, IgG3, IgG4, IgM, IgA1, IgA2, IgD and IgE antibodies. Antibody fragments include single-chain variable fragment (scFv), single chain antibodies, F(ab')$_2$ fragments, Fab fragments, and fragments produced by an Fab expression library, with the only limitation being that the antibody fragments retain the ability to bind the selected tag.

The antibodies may also be polyclonal, monoclonal, or chimeric antibodies, such as where an antigen binding region (e.g., F(ab')$_2$ or hypervariable region) of a non-human antibody is transferred into the framework of a human antibody by recombinant DNA techniques to produce a substantially human molecule. Antigen-binding fragments, such as scFv, may be prepared therefrom.

One advantage of the AT-CARs of the present invention is that they can be produced using commercially-available antibodies. Alternatively, antibodies to a selected tag may be produced. For the production of antibodies, various hosts including, but not limited to, goats, rabbits, rats, mice, humans, etc., can be immunized by injection with a particular protein or any portion, fragment, or oligopeptide that retains immunogenic properties of the protein. Depending on the host species, various adjuvants can be used to increase the immunological response. Such adjuvants include, but are not limited to, detoxified heat labile toxin from *E. coli*, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum* are also potentially useful adjuvants.

Antibodies and fragments thereof can be prepared using any technique that provides for the production of antibody molecules, such as by continuous cell lines in culture for monoclonal antibody production. Such techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci 80:2026-2030 (1983)), and the EBV-hybridoma technique (Cole et al., Monoclonal Antibodies and Cancer Therapy, Alan R. Liss Inc, New York N.Y., pp 77-96 (1985)).

Techniques developed for the production of "chimeric antibodies," i.e., the splicing of mouse antibody genes to human antibody genes to obtain a molecule with appropriate antigen specificity and biological activity, can also be used (Morrison et al., Proc Natl. Acad. Sci 81:6851-6855 (1984); Neuberger et al., Nature 312:604-608(1984); Takeda et al., Nature 314:452-454(1985)). Alternatively, techniques described for the production of single chain antibodies, such as disclosed in U.S. Pat. No. 4,946,778, incorporated herein by reference in its entirety, can be adapted to produce tag-specific single chain antibodies.

In one aspect, the tag-binding domain is a single-chain variable fragment (scFv). A scFv comprises the variable regions of the heavy (VH) and light chains (VL) of an antibody, typically linked via a short peptide of ten to about 25 amino acids. The linker can either connect the N-terminus of the VH with the C-terminus of the VL, or vice versa.

As indicated above, the binding specificity of the tag-binding domain will depend on the identity of the tag that is conjugated to the protein that is used to bind target cells. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv.

The second domain is a transmembrane (TM) domain. The TM domain allows the CAR to be anchored into the cell membrane of the T cell. Exemplary TM domains include, but are not limited to, the hinge and transmembrane regions of the human CD8α chain.

The third domain, when present, is the T cell activation domain. This domain aids in T cell activation upon binding of the CAR to the tagged protein that is bound to the target cell. T cell activation includes induction of cytokine and chemokine production, as well as activation of the cytolytic activity of the cells. Exemplary T cell activation domains include, but are not limited to, the cytoplasmic regions of CD28, CD137 (41BB), OX40 and HVEM which serve to enhance T cell survival and proliferation; and CD3ζ and FcRε which induce T cell activation. One or more than one T cell activation domain may be included in the CAR, such as two, three, four or more T cell activation domains.

AT-CAR T cell production. T cells may be engineered to express AT-CARs by means readily known to the skilled artisan. Generally, a polynucleotide vector is constructed that encodes the AT-CAR and the vector is transfected into a population of T cells. The cells are then grown under conditions promoting expression of the AT-CAR by the T cells. Successful transfection (or transduction which refers to viral-mediated gene integration) and display of AT-CARs by T cells is conducted via conventional means, some of which are disclosed in the Examples herein.

In one aspect, T cells may be engineered to produce AT-CARs by first constructing a retroviral vector encoding a selected AT-CAR. An exemplary retroviral vector includes, but is not limited to, the vector backbone pMSGV1-CD8-28BBZ, which is derived from pMSGV (murine stem cell virus-based splice-gag vector). DNA sequencing can be used to confirm proper construction of the vector before transfection of T cells. Retroviral transduction may be performed using known techniques, such as that of Johnson et al. (*Blood* 114, 535-546 (2009)). The surface expression of AT-CAR on transduced T cells may be determined, for example, by flow cytometry after staining cells with tag-conjugated protein or tag-conjugated dextran beads. The tag portion of the protein or beads will be bound by the tag-binding domain of the CAR expressed by the cells.

AT-CAR T cell administration. Populations of AT-CAR-expressing T cells may be formulated for administered to a subject using techniques known to the skilled artisan. Formulations comprising populations of AT-CAR-expressing T cells may include pharmaceutically acceptable excipient(s). Excipients included in the formulations will have different purposes depending, for example, on the nature of the tag-binding domain comprising the AT-CAR, the subpopulation of T cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The formulations comprising populations of AT-CAR-expressing T cells will typically have been prepared and cultured in the absence of any non-human components, such as animal serum (e.g., bovine serum albumin).

A formulation may include one population of AT-CAR-expressing T cells, or more than one, such as two, three, four, five, six or more populations of AT-CAR-expressing T cells. The different populations of AT-CAR T cells can vary based on the identity of the tag-binding domain, the identity of the activation domain, the identity of the subpopulation of T cells, or a combination thereof. For example, a formulation may comprise populations of AT-CAR-expressing T cells that recognize and bind to one, or more than one, such as two, three, four, five, six or more different tagged proteins. As an example, a formulation may comprise populations of AT-CAR-expressing T cells that recognize and bind FITC, biotin and PE. Thus, in this example, the formulation comprises three different populations of AT-CAR-expressing T cells that recognize and bind cells tagged by FITC-conjugated antibodies, biotin-conjugated antibodies, and PE-conjugated antibodies. This formulation would therefore comprise αFITC-CAR-expressing T cells, αbiotin-CAR-expressing T cells and αPE-CAR-expressing T cells.

The formulations comprising population(s) of AT-CAR T cells may be administered to a subject using modes and techniques known to the skilled artisan. Exemplary modes include, but are not limited to, intravenous injection. Other modes include, without limitation, intratumoral, intradermal, subcutaneous (s.c., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of the formulations can be used to effect such administration.

The formulations comprising population(s) of AT-CAR-expressing T cells that are administered to a subject comprise a number of AT-CAR-expressing T cells that is effective for the treatment and/or prophylaxis of the specific indication or disease. Thus, therapeutically-effective populations of AT-CAR-expressing T cells are administered to subjects when the methods of the present invention are practiced. In general, formulations are administered that comprise between about $1 \times 10^4$ and about $1 \times 10^{10}$ AT-CAR-expressing T cells. In most cases, the formulation will comprise between about $1 \times 10^5$ and about $1 \times 10^9$ AT-CAR-expressing T cells, from about $5 \times 10^5$ to about $5 \times 10^8$ AT-CAR-expressing T cells, or from about $1 \times 10^6$ to about $1 \times 10^7$ AT-CAR-expressing T cells. However, the number of AT-CAR-expressing T cells administered to a subject will vary between wide limits, depending upon the location, source, identity, extent and severity of the cancer, the age and condition of the individual to be treated, etc. A physician will ultimately determine appropriate dosages to be used.

Tagged proteins. Tagged proteins are administered to a subject prior to, or concurrent with, or after administration of the AT-CAR-expressing T cells. The tagged proteins bind to target cells in the subject. In general, the "protein" portion of the tagged protein is the portion of the molecule that binds to the target cell. For example, the protein may be an antibody that binds to a tumor-associated antigen (TAA) or a tumor specific antigen (TSA) expressed by the target cell. However, the "protein" may be any molecule that binds to a target cell. Exemplary proteins include, but are not limited to, anti-cancer-based monoclonal antibodies such as cetuximab (anti-EGFR), nimotuzumab (anti-EGFR), panitumumab (anti-EGFR), retuximab (anti-CD20), omalizumab (anti-CD20), tositumomab (anti-CD20), trastuzumab (anti-Her2), gemtuzumab (anti-CD33), alemtuzumab (anti-CD52), and bevacizumab (anti-VEGF).

The "tag" portion of the tagged protein is only constrained by being a molecular that can be recognized and specifically bound by the AT-CAR, specifically, the tag-binding domain of the AT-CAR. Exemplary tags include, but are not limited to, fluorescein isothiocyanate (FITC), dinitrophenol, peridinin chlorophyll protein complex, green fluorescent protein, biotin, phycoerythrin (PE), histidine, streptavidin, horse radish peroxidase, palmitoylation, nitrosylation, alkalanine phosphatase, glucose oxidase, Glutathione S-transferase, maltose binding protein, and any types of fluorescent materials including quantum dot nanocrystals.

Thus, in some aspects, the tagged proteins include FITC-conjugated antibodies, biotin-conjugated antibodies, PE-conjugated antibodies, histidine-conjugated antibodies and streptavidin-conjugated antibodies, where the antibody binds to a TAA or a TSA expressed by the target cells. For example, the tagged proteins of the present invention include, but are not limited to, FITC-conjugated cetuximab, FITC-conjugated retuximab, FITC-conjugated herceptin, biotin-conjugated cetuximab, biotin-conjugated retuximab, biotin-conjugated herceptin, PE-conjugated cetuximab, PE-conjugated retuximab, PE-conjugated herceptin, histidine-conjugated cetuximab, histidine-conjugated retuximab, histidine-conjugated herceptin, streptavidin-conjugated cetuximab, streptavidin-conjugated retuximab, and streptavidin-conjugated herceptin. Alternatively, the AT-CAR cells can be redirected to target and/or destroy vascular cells feeding the tumor. For example, T cells expressing αFITC-VEGF as the AT-CAR can target endothelial vascular cells to which FITC-tagged VEGF is bound, where the FITC-tagged VEGF is bound by the VEGF receptor.

In some aspects, a protein lacking a tag may be used as the tagged protein. For example, a naked (tagless) protein (such as an antibody) that binds to a TAA or a TSA on a target cell may be used as the tagged protein. Under such circumstances, the AT-CAR will recognize and specifically bind the protein. As an example, the tag-binding domain may be an antibody or antigen-binding fragment thereof that recognizes and binds a second antibody, where the second antibody functions as the tagged protein and where the second antibody lacks a tag.

The tag may be conjugated to the proteins using techniques such as chemical coupling and chemical cross-linkers. Alternatively, polynucleotide vectors can be prepared that encode the tagged proteins as fusion proteins. Cell lines can then be engineered to express the tagged proteins, and the tagged proteins can be isolated from culture media, purified and used in the methods disclosed herein.

The tagged proteins may be formulated for administered to a subject using techniques known to the skilled artisan. Formulations of the tagged proteins may include pharmaceutically acceptable excipient(s). Excipients included in the formulations will have different purposes depending, for example, on the nature of the tag, the protein, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents.

A formulation of tagged proteins may include one type of tagged protein, or more than one, such as two, three, four, five, six or more types of tagged proteins. The different types of tagged proteins can vary based on the identity of the tag, the identity of the protein, or both. For example, a formulation comprising three types of tagged protein might include FITC-conjugated cetuximab, FITC-conjugated rituximab and FITC-conjugated herceptin, or FITC-conjugated cetuximab, biotin-conjugated cetuximab, and PE-conjugated cetuximab.

The tagged proteins may be administered to a subject using modes and techniques known to the skilled artisan. Exemplary modes include, but are not limited to, intravenous, intraperitoneal, and intratumoral injection. Other modes include, without limitation, intradermal, subcutaneous (s.c., s.q., sub-Q, Hypo), intramuscular (i.m.), intra-arterial, intramedullary, intracardiac, intra-articular (joint), intrasynovial (joint fluid area), intracranial, intraspinal, and intrathecal (spinal fluids). Any known device useful for parenteral injection or infusion of the formulations can be used to effect such administration.

Formulations comprising the tagged proteins are administered to a subject in an amount which is effective for treating and/or prophylaxis of the specific indication or disease. In general, formulations comprising at least about 0.1 mg/kg to about 100 mg/kg body weight of the tagged proteins are administered to a subject in need of treatment. In most cases, the dosage is from about 1 mg/kg to about 10 mg/kg body weight of the tagged proteins daily, taking into account the routes of administration, symptoms, etc. As an example, tagged-bevacizumab is administered in a dosage of from about 2.5 to about 5 mg/kg. As a further example, tagged-cetuximab is administered in a dosage ranging from about 100 to about 400 mg/m$^2$. However, the amount of tagged protein in formulations administered to a subject will vary between wide limits, depending upon the location, source, identity, extent and severity of the cancer, the age and condition of the individual to be treated, etc. A physician will ultimately determine appropriate dosages to be used.

Cancer. The present invention relates to methods of treating a subject having cancer, comprising administering to a subject in need of treatment one or more formulations of tagged proteins, wherein the tagged proteins bind a cancer cell, and administering one or more therapeutically-effective populations of AT-CAR-expressing T cells, wherein the AT-CAR-expressing T cells bind the tagged proteins and induce cancer cell death. The term "cancer" is intended to be broadly interpreted and it encompasses all aspects of abnormal cell growth and/or cell division. Examples include: carcinoma, including but not limited to adenocarcinoma, squamous cell carcinoma, adenosquamous carcinoma, anaplastic carcinoma, large cell carcinoma, small cell carcinoma, and cancer of the skin, breast, prostate, bladder, vagina, cervix, uterus, liver, kidney, pancreas, spleen, lung, trachea, bronchi, colon, small intestine, stomach, esophagus, gall bladder; sarcoma, including but not limited to chondrosarcoma, Ewing's sarcoma, malignant hemangioendothelioma, malignant schwannoma, osteosarcoma, soft tissue sarcoma, and cancers of bone, cartilage, fat, muscle, vascular, and hematopoietic tissues; lymphoma and leukemia, including but not limited to mature B cell neoplasms, such as chronic lymphocytic leukemia/small lymphocytic lymphoma, B-cell prolymphocytic leukemia, lymphomas, and plasma cell neoplasms, mature T cell and natural killer (NK) cell neoplasms, such as T cell prolymphocytic leukemia, T cell large granular lymphocytic leukemia, aggressive NK cell leukemia, and adult T cell leukemia/lymphoma, Hodgkin lymphomas, and immunodeficiency-associated lymphoproliferative disorders; germ cell tumors, including but not limited to testicular and ovarian cancer; blastoma, including but not limited to hepatoblastoma, medulloblastoma, nephroblastoma, neuroblastoma, pancreatoblastoma, leuropulmonary blastoma and retinoblastoma. The term also encompasses benign tumors.

As used herein, the terms "treat", "treating", and "treatment" have their ordinary and customary meanings, and include one or more of: blocking, ameliorating, or decreasing in severity and/or frequency a symptom of cancer in a subject, and/or inhibiting the growth, division, spread, or proliferation of cancer cells, or progression of cancer (e.g., emergence of new tumors) in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

Administration frequencies of both formulations comprising populations of AT-CAR-expressing T cells and formulations of tagged proteins will vary depending on factors that include the disease being treated, the elements comprising the AT-CAR-expressing T cells and the tagged proteins, and the modes of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The duration of treatment will be based on the disease being treated and will be best determined by the attending physician. However, continuation of treatment is contemplated to last for a number of days, weeks, or months.

The present invention offers flexibility in the methods of treatment, and as a result, the formulation(s) of tagged proteins and the population(s) of AT-CAR-expressing T cells may be administered to a subject in any order. Thus, the formulation(s) of tagged proteins may be administered to a subject before, after or concurrently with the population(s) of AT-CAR-expressing T cells. Alternatively, where more than one formulation of tagged proteins and/or more than one population of AT-CAR-expressing T cells are administered to a subject, the administration can be staggered. For example, a first formulation of tagged proteins can be administered, followed by a first population of AT-CAR-expressing T cells, which is then followed by a second formulation of tagged proteins and then a second population of AT-CAR-expressing T cells.

The present invention also includes methods whereby a population of AT-CAR-expressing T cells is coated with tagged proteins prior to administration of the AT-CAR-expressing T cells to the subject.

In each of the embodiments of the present invention the subject receiving treatment is a human or non-human animal, e.g., a non-human primate, bird, horse, cow, goat, sheep, a companion animal, such as a dog, cat or rodent, or other mammal.

The invention also provides a kit comprising one or more containers filled with one or more populations of AT-CAR-expressing T cells and one or more formulations of tagged proteins. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

IV. Examples

Mice and cell lines. NOD-scid IL2Rgamma$^{null}$ (NSG) mice were purchased from the Jackson Laboratory (Bar Harbor, ME, USA), housed in the University of Maryland, Baltimore, specific pathogen-free animal facility and used as recipients for adoptive immunotherapy. Experiments were reviewed and approved by the University of Maryland Baltimore Institutional Animal Care and Use Committee. The human EGFR+ colon adenocarcinoma cell line SW480 (ATCC, Manassas, VA) was maintained in Dulbecco's modified Eagle's medium (DMEM) (GIBCO brand; Invitrogen, Carlsbad, CA, USA) supplemented with 10% heat inactivated fetal bovine serum (Gemini Bio-Products, West Sacramento, CA, USA), 2 mM L-glutamine (GIBCO brand; Invitrogen) and 1% penicillin-streptomycin (GIBCO brand; Invitrogen). The EGFR+ HER2+ pancreatic adenocarcinoma cell line Panc 6.03 was kindly provided by Dr. Elizabeth Jaffee (Sidney Kimmel Cancer Center at Johns Hopkins), and cultured in RPMI 1640 medium (GIBCO brand; Invitrogen) supplemented with 20% FBS, 1% MEM non-essential amino acids (GIBCO brand; Invitrogen), 1% sodium pyruvate (GIBCO brand; Invitrogen), 2 mM L-glutamine, 1% penicillin-streptomycin and 100 IU/ml insulin. The HER-2+ breast adenocarcinoma cell line AU565 (ATCC) was cultured in RPMI 1640 medium supplemented with 10% FBS, 2 mM L-glutamine and 1% penicillin-streptomycin. The Phoenix Ampho packaging cell line was purchased from Orbigen (San Diego, CA, USA) and maintained in D10 medium containing DMEM, 10% FBS, 1% sodium pyruvate, 2 mM L-glutamine and 1% penicillin-streptomycin. The surface expression of EGFR or HER2 on SW480, Panc 6.03 and AU565 cell lines was determined by flow cytometry using FITC-conjugated Cetuximab (Ctx) or FITC-conjugated Herceptin (Her2).

Figure 1:
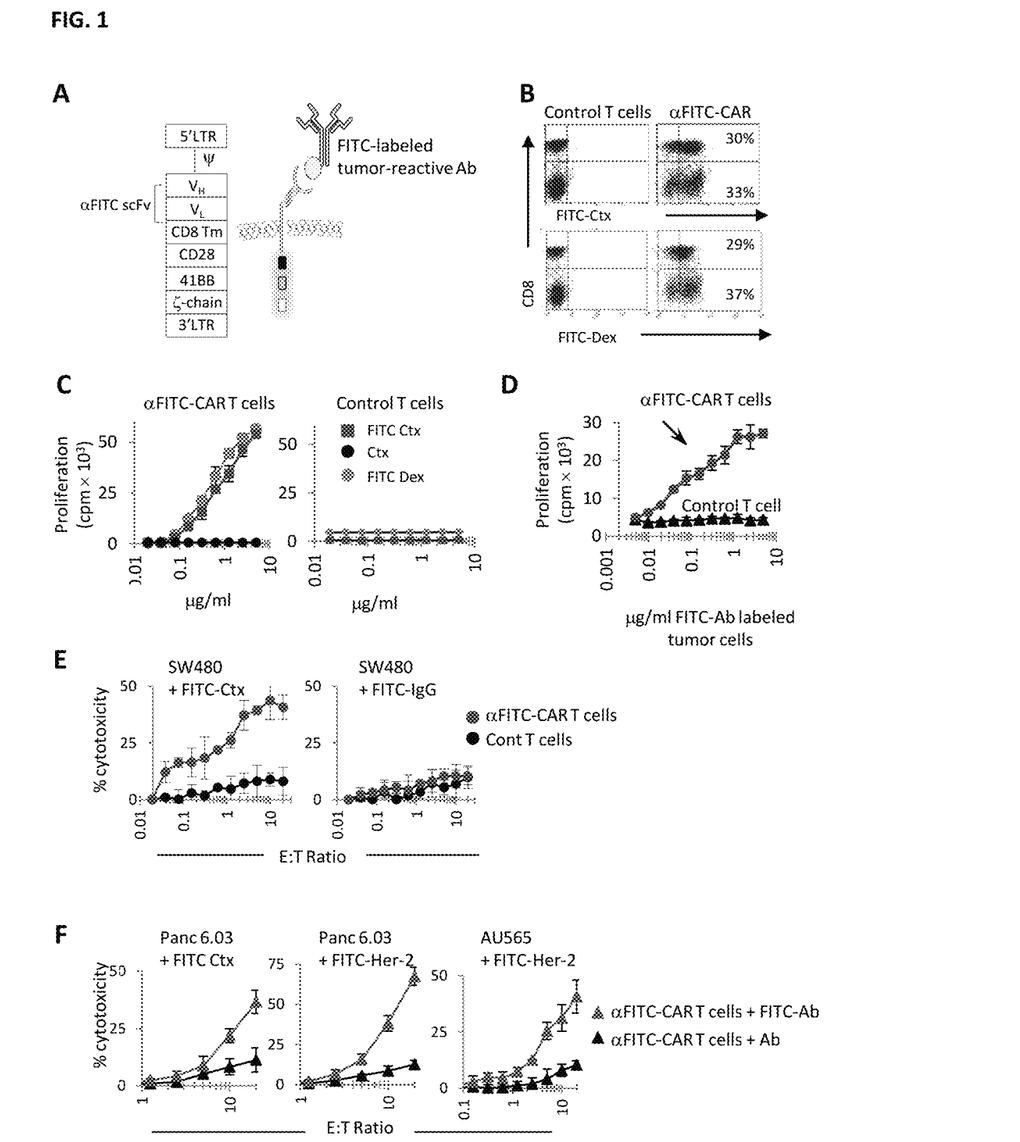

Construction of retroviral vector. The retroviral vector backbone pMSGV1-CD8-28BBZ (Hughes M. S. et al., Transfer of a TCR gene derived from a patient with a marked antitumor response conveys highly active T-cell effector functions. Hum Gene Ther 2005 April; 16(4):457-72) was a kind gift from Dr. Richard Morgan (National Cancer Institute) and is derived from pMSGV (murine stem cell virus-based splice-gag vector). FIG. 1A shows schematically representation of the vector construct, and the order of placement of components in-frame from the 5' to the 3' ends. The mouse scFv against FITC is referred to as αFITC-CAR and is linked to the hinge and transmembrane regions of the human CD8α chain (nucleotide sequence 1271-1519, Genbank NM 001768.6), and the cytoplasmic regions of the human CD28 (nucleotide sequence 760-882, Genbank NM 006139.2), 4-1BB (nucleotide sequence 886-1026, Genbank NM 001561.5) and CD3 (nucleotide sequence 299-637, Genbank NM 000734.3) molecules. The αFITC-CAR sequence was synthesized by BlueHeron (Bothell, WA).

The sequence was confirmed by DNA sequencing and has the following sequence: agttgcctgttaggttgttggtgctgatgttctg-gattectgatccagcagtgatgtcgtgatgacccaaactc-cactctccctgcctgtcagtct tggagatcaagcctccatcttgca-gatctagtcagagccttgtacacagtaatggaaacacctatttacgttggtacctgca gaagccagg ccagtctccaaaggtctgatctacaaagtttccaaccgat-tttctggggtcccagacaggttcagtggcagtggatcagggacagatttcac act-caagatcagcagagtggaggctgaggatctgggagtttatttctgctctcaaagta-cacatgttccgtggacgtteggtggaggcacca agctggaaatcaaagtagtgctgat-gatgctaagaaggatgctgctaagaaggatgatgctaagaaggat-gatgctaagaaggatggtga ggtgaagctggatgagactggaggag-gettggtgcaacctgggaggcccatgaaactctctgtgttgcctctggattcacttt agtgacta ctgatgaactgggtccgccagtctccagagaaaggactg-gagtgggtagcacaaattagaaacaaaccttataattatgaaacatattatte agat-tctgtgaaaggcagattcaccatctcaagagatgattccaaaagtagtgtc-tacctgcaaatgaacaacttaagagttgaagacatggg tatctattactgtacgggttatactatggtatggactactggggt-caaggaacctcagtcaccgtctcc (SEQ ID NO:1). The sequence was ligated into pMSGV1 to generate the αFITC-CAR retroviral vector.

Retroviral transduction of human T cells. HLA-A2+ peripheral blood mononuclear cells (PBMC) from healthy donors were purchased from Biological Specialty Corp (Colmar, PA, USA), and isolated by Ficoll-Pague (GE Healthcare, Piscataway, NJ, USA) density gradient centrifugation. Isolated PBMC were cultured at $3 \times 10^6$ per well in 24-well tissue culture plates in AIM V medium (GIBCO brand; Invitrogen) supplemented with 5% human AB serum (Sigma-Aldrich), 1% MEM non-essential amino acids, 1% penicillin-streptomycin and 100 U/ml recombinant human IL-2 (BioLegend, San Diego, CA, USA), and activated with 50 ng/ml OKT3 (eBioscience, San Diego, CA, USA). Two days later, cells were collected for retroviral transduction. For transduction, 24-well non-tissue culture treated plates (BD Biosciences, Franklin Lakes, NJ, USA) were coated with 0.5 ml per well of 10 µg/ml recombinant human fibronectin fragment (RetroNectin; Takara, Otsu, Shiga, Japan) overnight at 4° C. After incubation, wells were blocked with 1 ml of Hanks's balanced salt solution (GIBCO brand; Invitrogen) plus 2.5% human AB serum for 30 min at RT, and washed with Hanks's balanced salt solution plus 2.5% N-2-hydroxyethylpiperazine-N'-2-ethanesulfonic acid (HEPES) (GIBCO brand; Invitrogen). Transductions were conducted as previously described (Johnson et al. *Blood* 114, 535-546 (2009)). Briefly, approximately 2.5 ml of retroviral supernatant were added to each coated well followed by centrifugation at 2000 g for 2 h at 32° C. 1.5 ml of viral supernatant was removed and $1 \times 10^6$ (0.5 ml) activated PBMC were added to each well in the presence of 100 U/ml IL-2. Plates were centrifuged at 1000 g for 10 min, and then incubated overnight at 37° C. After transduction, cells were washed and maintained in the presence of IL-2 (100 U/ml) and used in experiments five days after transduction. The surface expression of αFITC-CAR on transduced human T cells was determined by flow cytometry after staining cells with CD3 or CD8 and FITC-conjugated cetuximab. In some experiments, αFITC-CAR transduced T cells were stained with FITC-conjugated dextran beads. Cells stained with FITC-conjugated purified human IgG (Invitrogen) were used as an isotype control.

T cell proliferation assay, cytokine and chemokine production assay. Three to five days after transduction, $1 \times 10^5$ T cells were cultured in 96-well round-bottom plates coated with cetuximab, FITC-conjugated cetuximab, or FITC-Dextran for 72 h. For T cell specific reactivity against tumor cells, SW480 cells were pulsed with the indicated concentrations of antibodies for 1 h at 37° C., washed 3 times. $1 \times 10^5$ effector T cells and $1 \times 10^5$ tumor cells were co-cultured in 200 µl of culture volume in 96-well round-bottom plates for 72 h. Sixteen hours before harvesting, 0.5 µCi of 3H-thymidine was added to each well prior to measuring thymidine uptake using a 1450 LSC & luminescence counter (PerkinElmer, Waltham, MA, USA). Cytokine and chemokine production levels were measured from culture supernatants collected 48 hours after stimulation using a Cytokine/Chemokine kit (Millipore, Billerica, MA, USA) according to manufacturer's instructions. In some experiments, tumor explants were finely minced and cultured in trypsin for 2 hours at 37° C. followed by T cell enrichment using a negative selection kit (Invitrogen/Life Technologies, Grand Island, NY). 200,000 T cells were co-cultured with SW480 (50,000) colon cancer cells which had been pulsed with FITC-Ctx or Ctx (0.5 µg/$1 \times 10^6$ cells). Three days later proliferation was determined by [$^3$H]thymidine uptake (±SD) or cytokine and chemokine production was measured using a Milliplex array.

Cytotoxicity assay. Cytotoxic activity against tumor target cells was measured using a standard 51 Cr release assay. $1 \times 10^6$ target cells were labeled with 200 µCi of 51 Cr for 2 h at 37° C., washed 3 times, and pulsed with anti-human antibodies for 1 h at 37° C. $1 \times 10^4$ labeled target cells were then co-cultured with decreasing numbers of effector T cells at the indicated effector to target (E:T) ratios in 200 µl of culture volume in 96-well round-bottom plates. Target cells incubated in medium alone were used to determined spontaneous 51 Cr release, and maximal release was determined by incubating labeled target cells in 10% Triton X-100. After 5 hours at 37° C., 50 µl of supernatant was collected and 51 Cr radioactivity was measured in a 1450 LSC & luminescence counter. The mean percentage of specific lysis was calculated according to the following equation: % specific lysis=(test release−spontaneous release)/(maximal release−spontaneous release)×100. All tests were performed in triplicate wells and results are shown as mean±SD.

Tumor models and adoptive immunotherapy. In prophylactic tumor models 6- to 8-wk-old male NSG mice (n=5 for each group) were injected subcutaneously (s.c.) in the rear leg flank with $1-2 \times 10^6$ SW480 or Panc 6.03 tumor cells. One day later mice were injected intraperitoneally (i.p.) with FITC-Ctx or Ctx (25 µg/mouse). One day after Ctx injection, mice were injected intravenous (i.v.) with $5 \times 10^6$ αFITC-CAR transduced human T cells. After adoptive T cells transfer, mice were injected i.p. with antibodies (25 µg/mouse) weekly for three weeks. Tumor area was measured with digital calipers in a blinded manner two to three times per week, and tumor sizes (mm$^2$) were calculated by perpendicular measurement by longitudinal diameter. Mice were euthanized when tumor sizes reach 200 mm$^2$ or if mice became moribund or had trouble ambulating. All experiments were performed independently at least twice with similar results. Survival data were analyzed with the exact long-rank test.

Experiment 1. Peripheral blood mononuclear cells were activated with anti-CD3 mAb in the presence of IL-2 followed by transduction with the α-FITC-CD28-41BB-CD3ζ-CAR vector (referred to as αFITC-CAR) as shown in FIG. 1A and as described above. The expression of the αFITC scFv on T cells was analyzed by staining cells with anti-CD8 (or anti-CD3) and FITC-labeled cetuximab (FITC-Ctx) or FITC-labeled dextran (FITC-Dex) beads. On average, 60% of total T cells expressed αFITC-CAR (FIG. 1B). To confirm their functionality and specificity, αFITC-CAR or control (mock transduced) T cells were activated using titrating concentrations of plate-bound FITC-Ctx, unbound cetuximab, or FITC-Dex beads. αFITC-CAR T cells proliferated vigorously and in a dose dependent manner following stimulation with FITC-Ctx and FITC-Dex but did not divide in response to stimulation with Ctx alone (FIG. 1C, left panel). In contrast, control T cells did not proliferate to FITC-Ctx or FITC-Dex (FIG. 1C, right panel). T cells were also co-cultured with EGFR colon cancer cells (SW480) which had been stained with titrating concentrations of FITC-Ctx. FITC reactivity by αFITC-CAR T cells was demonstrated by their ability to divide following activation with FITC-Ctx-stained cancer cells, FIG. 1D. However, proliferation was similar to that of control at the lowest concentrations of FITC-Ctx. Control T cells did not proliferative in response to any concentration of FITC-Ctx-stained cancer cells, FIG. 1D.

To determine their cytolytic capacity, αFITC-CAR T cells were cultured together with FITC-Ctx-stained SW480 colon cancer cells at various effector to target ratios. αFITC-CAR T cells lysed SW480 colon cancer cells at effector to target ratios as low as one T cell to twenty target cells (FIG. 1E, left panel) but did not lyse cancer cells labeled with FITC-mouse IgG (FIG. 1E, right panel). Similarly, control T cells did not show an appreciable level of cytolytic activity against FITC-Ctx-labeled or FITC-IgG—labeled SW480 cancer cells (FIG. 1E). To confirm their ability to recognize a variety of target cells expressing different antigens αFITC-CAR T cells were co-cultured with pancreatic cancer cells (Panc 6.03) stained with FITC-Ctx or stained with FITC-Herceptin (anti-Her-2 mAb; FITC-Her2) and breast cancer cells (AU565) stained with FITC-Her2. αFITC-CAR T cells efficiently and specifically lysed cancer cells stained with FITC-Ctx or FITC-Her2 (FIG. 1F). It is worth noting that the increased cytolytic activity against FITC-Her2-stained pancreatic cancer cells above cells stained with FITC-Ctx is likely associated with the higher expression level Her-2 as compared with EGFR (data not shown). Furthermore, αFITC-CAR T cells produced a wide array of cytokines beneficial to T cell survival, expansion and chemotaxis (Table 1). The background cytokine levels produced by control T cells activated with FITC-Ctx- or Ctx-stained cancer cells were identical to one another.

TABLE 1

Cytokines and chemokine production by αFITC-CAR T cells. HLA-A2$^+$ PBMCs were activated with anti-CD3 antibodies in the presence of IL-2 followed by transduction with αFITC-CAR retrovirus. αFITC-CAR functionality on transduced was determined by their ability to produce cytokines and chemokines following activation with SW480colon cancer cells that were stained with FITC-Ctx or Ctx. The levels of various cytokines and chemokines produced by α-FITC-CAR T cells were measured 72 hours after stimulation using a Milliplex cytokine/chemokine array. These data are representative of three independent experiments (three different donors) with each experiment yielding the same trends.

|  | +Ctx | +FITC-Ctx | Fold change |
|---|---|---|---|
| FGF-2 | 1.9 ± (0.79) | 15.8 ± (2.59) | 8.1 |
| GM-CSF | 45.7 ± (5.26) | 2803.3 ± (57.74) | 61.2 |
| IL-2 | 13.4 ± (2.6) | 193 ± (8.5) | 14.4 |
| IL-3 | 1.1 ± (0.22) | 31.4 ± (6.50) | 26.5 |
| IL-5 | 1.7 ± (0.01) | 6.3 ± (0.07) | 3.6 |
| IL-7 | 0.7 ± (0.64) | 2.2 ± (0.32) | 3.0 |
| IL-9 | 0.6 ± (1.06) | 1.8 ± (0.25) | 2.9 |
| IL-12 p70 | 0.3 ± (0.59) | 1.0 ± (0.10) | 3.1 |
| IL-13 | 0.3 ± (0.62) | 311.6 ± (6.51) | 873.8 |
| IL-17 | 16.6 ± (2.15) | 644.6 ± (20.84) | 38.6 |
| sIL-2Ra | 61.4 ± (5.18) | 919.6 ± (59.03) | 14.9 |
| sCD40L | 27.6 ± (5.92) | 1406.6 ± (158.22) | 50.90 |
| IFN-γ | 4.3 ± (0.98) | 2906.6 ± (162.58) | 662.1 |
| TNF-α | 4.5 ± (0.41) | 395.6 ± (33.26) | 87.8 |
| TNF-β | 1.3 ± (0.10) | 81.1 ± (7.71) | 61.4 |
| MCP-1 (CCL2) | 5.1 ± (0.53) | 2243.3 ± (284.31) | 437.8 |
| MIP-1α (CCL3) | 6.7 ± (0.89) | 3234.3 ± (225.02) | 483.8 |
| MIP-1β (CCL4) | 7.8 ± (1.39) | 986.3 ± (40.99) | 125.3 |
| RANTES (CCL5) | 0 | 778.3 ± (66.37) | 778 |
| MCP-3 (CCL7) | 2.0 ± (1.77) | 194.3 ± (4.73) | 94.9 |
| MDC (CCL22) | 136.3 ± (13.65) | 6503.3 ± (551.75) | 47.7 |
| Eotaxin (CCL11) | 3.2 ± (1.29) | 32.1 ± (3.56) | 9.8 |
| IP-10 (CXCL10) | 14.9 ± (1.60) | 14166.6 ± (1484.3) | 950.7 |

Collectively, these data demonstrate: 1) the functionality of αFITC-CAR T cells, 2) their specificity against FITC-Ab-stained cells but not soluble FITC, 3) their ability to lyse a diverse set tumor cell types, and 4) the use of various FITC-tagged antibodies.

Figure 2:
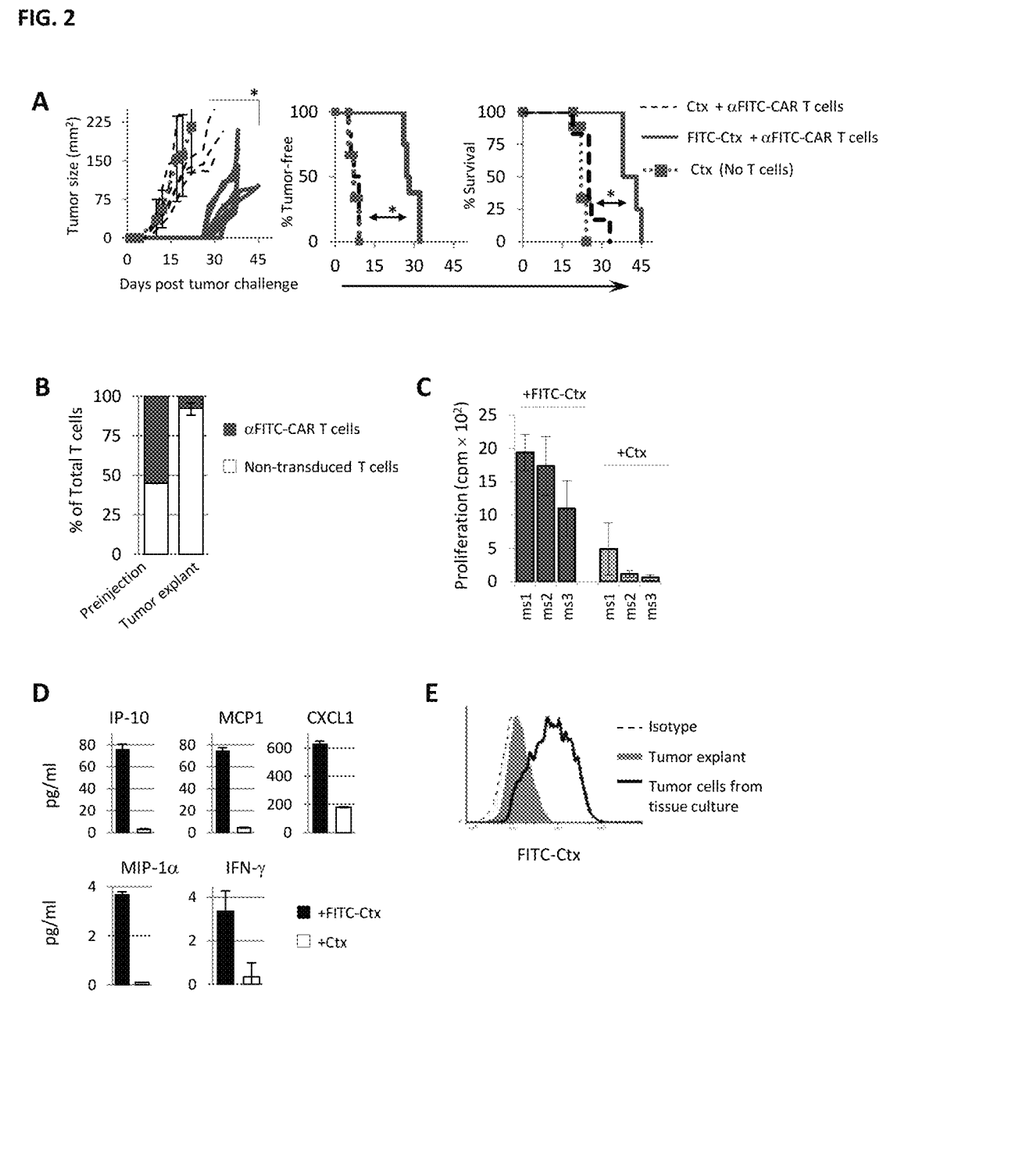

Experiment 2. The ability to re-direct αFITC-CAR T cells to eliminate tumor cells in vivo was examined. Mice were injected s.c. with SW840 colon cancer cells followed by the administration of FITC-Ctx or Ctx via i.p. injection. One day later αFITC-CAR T cells were administered via i.v. injection into the tail vein. Tumor growth kinetics was similar between mice receiving αFITC-CAR T cells plus Ctx and those receiving Ctx alone, FIG. 2A left panel. In sharp contrast, tumor growth was greatly suppressed in mice receiving αFITC-CAR T cells plus FITC-Ctx (FIG. 2A left panel). Likewise, the tumor-free occurrence (FIG. 2A middle panel) and overall survival (FIG. 2A right panel) was significantly improved in mice receiving αFITC-CAR T cells plus FITC-Ctx as compared with control groups. In spite of this survival advantage however, mice receiving α-ITC-CAR T cells plus FITC-Ctx succumbed to tumor challenge within 55 days of tumor implantation.

The mechanisms contributing to the failure of αFITC-CAR T cells in long-term treatment were further investigated. Because T cells were activated with CD3 mAb and IL-2, CAR T cells can display a shortened life despite receiving prosurvival signals from CD28 or 41BB (Sadelain et al. *Curr. Opin. Immunol.* 21, 215-223 (2009); Brentjens et al. *Nat. Med.* 9, 279-286 (2003)). The presence of αFITC-CAR T cells in various tissues was assayed, including the spleen, liver, bone marrow, circulation and in tumor explants. αFITC-CAR T cells were found in all tissues analyzed. Approximately 10% of all human T cells detected in tumor explants were αFITC-CAR T cells, FIG. 2B. Similar percentages were found in the other tissues (data not shown). However, the overall percentage of αFITC-CAR T cells at the time of organ collection (between days 38 and 45) was significantly lower than the starting percentage of 60% at infusion. It is also worth noting that 60% to 90% of the T cells recovered from mice were CD8$^+$, as compared with the starting percentage of 40-50%. These data suggest a potential survival advantage of CD8$^+$ subset over CD4$^+$ T cells in vivo. The frequency or role for CD4 T$_{Regs}$ was not examined but remains a viable option that merits further investigation.

Alternatively, αFITC-CAR T cells might not have become sufficiently activated by antigen (FITC) perhaps due to anergy or other suppressive mechanisms. Total T cells were enriched from the tumor explant and immediately reactivated using SW480 cells from tissue culture that were stained with FITC-Ctx or Ctx alone. αFITC-CAR T cells proliferated (FIG. 2C) and produced various effector molecules and chemokines (FIG. 2D) following stimulation with FITC-Ctx-stained SW480 cells but did not respond to SW480 cells stained with Ctx. Unfortunately, the numbers of αFITC-CAR T cells isolated from tumor explants were not sufficient to test their killing aptitude. However, based on their ability to divide and produce effector molecules ex vivo, α-FITC-CAR T cells are clearly capable of responding to FITC stimulation.

Based on the observations that α-FITC-CAR were present in mice and were responsive to FITC-CAR stimulation, EGFR expression on tumor explants was examined. As examined by flow cytometry, all tumor explants were completely devoid of EGFR expression as compared with isotype control and with SW480 cells taken from tissue culture (FIG. 2E). In addition, although the majority of SW480 cells taken from tissue culture expressed EGFR, its expression was heterogeneous with some cells lacking EGFR.

Taken together, these data support the contention that αFITC-CAR killed EGFR cells but in time allowed the growth of EGFR cells which were no longer a target for αFITC-CAR T cells. The lack of EGFR expression, and therefore lack of FITC-mediated stimulation, might have also contributed to the lower frequency of αFITC-CAR T cells observed at later time points in tumor-bearing mice as compared with the percentage of αFITC-CAR T cells prior to injection. Additionally, these data highlight the potential for tumor escape occurring in patients in whose TAA is heterogeneously expressed. These studies also emphasize the potential need to use CAR T cells with specificity to several TAAs. One advantage to the use of an anti-tag CAR T cells is the potential to use several FITC 'tagged' tumor-reactive antibodies simultaneously. Alternatively, the use of CARs expressing scFvs specific for biotin or PE-conjugated antibodies would add to the diversity of anti-tag CARs.

Figure 3:
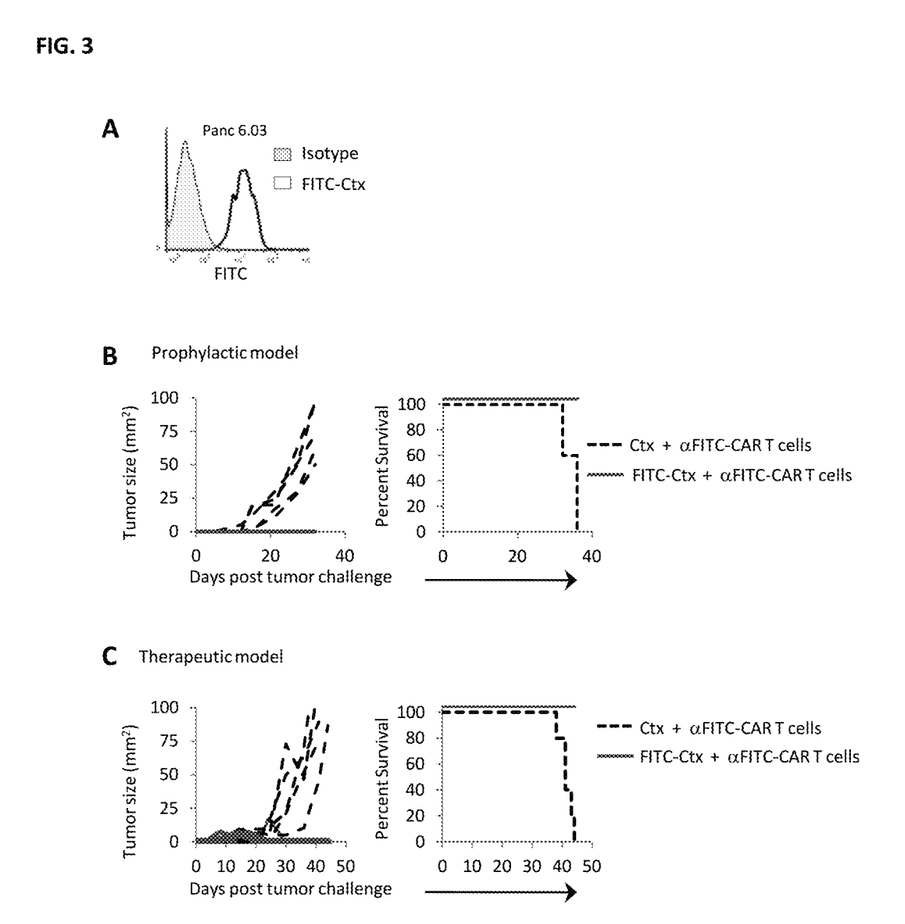

Experiment 3. Given the heterogeneity of EGFR expression on SW480 cancer cells, the ability of αFITC-CAR T cells to destroy a population of cancer cells in which all of the cells expressed the antigen was examined. The pancreatic cancer cell line Panc 6.03 was selected as the cells uniformly express EGFR (FIG. 3A). The cytolytic activity of αFITC-CAR T cells was examined in a prophylactic tumor model using the same procedure described in Experiment 2. Tumor growth was clearly suppressed in mice receiving αFITC-CAR T cells plus FITC-Ctx whereas mice receiving α-FITC-CAR T cells plus Ctx demonstrated rapid tumor growth, FIG. 3B left panel. All mice receiving αFITC-CAR T cells plus Ctx succumbed to tumor challenge within 35 days of tumor implantation, FIG. 3B right panel. It is worth noting that the administration of FITC-Ctx via i.v., i.p., or intratumoral injection all resulted in antibody localization to the tumor (data not shown). An alternative method to redirecting T cells to the tumor is to coat αFITC-CAR T cells with FITC-Ctx prior to adaptive transfer.

Experiment 4. The ability of αFITC-CAR T cells to destroy an established pancreatic tumor was examined. Pancreatic tumors were grown to sizes between 3-10 mm$^2$ when tumors were well-vascularized and then injected (i.p.) with FITC-Ctx or Ctx. One day later mice were administered αFITC-CAR T cells via tail vein injection. T cells with redirected specificity for EGFR eradicated established pancreatic tumors in all mice (FIG. 3C left panel) and improved survival as compared with mice treated with Ctx and αFITC-CAR T cells (FIG. 3C right panel). No tumor relapse occurred during the time of observation.

In summary, these studies are the first to describe the generation of a universal and adaptable CAR system which confers T cells specificity to FITC-tagged antibodies which when bound to various cancer types mediate tumor destruction. This report is also the first to emphasize the importance of using CAR T cells to target more than one TAA as TAA-negative tumor variants can arise and eventually kill the host. The platform is considered an 'off'-the-shelf system that considerably advances the existing CAR technology through its potential to target an assortment of tagged proteins (i.e., antibodies) in order to target various cancer types.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

What is claimed is:

1. A method of treating cancer in a subject, comprising:
   (a) administering a formulation of tagged proteins to a subject in need of treatment, wherein the tagged proteins bind a cancer cell in the subject, and
   (b) administering a therapeutically-effective population of anti-tag chimeric receptor (AT-CAR)-expressing effector cells to the subject, wherein the AT-CAR comprises a tag-binding domain, a transmembrane domain, and a T cell activation domain, where the T cell activation domain consists of one or more of the cytoplasmic region of OX40, the cytoplasmic region of HVEM, and FcRε, where the T cell activation domain does not comprise CD3ζ, and wherein the AT-CAR-expressing effector cells bind the tagged proteins and induce cancer cell death, thereby treating cancer in a subject.

2. A method of treating cancer in a subject, comprising:
   (a) administering one or more formulations of tagged proteins to a subject in need of treatment, wherein the tagged proteins bind a cancer cell in the subject, and
   (b) administering one or more therapeutically-effective populations of AT-CAR-expressing effector cells to the subject, wherein the AT-CAR comprises a tag-binding domain, a transmembrane domain, and a T cell activation domain, where the T cell activation domain consists of one or more of the cytoplasmic region of OX40, the cytoplasmic region of HVEM, and FcRε, where the T cell activation domain does not comprise CD3ζ, and wherein the AT-CAR-expressing effector cells bind the tagged proteins and induce cancer cell death, thereby treating cancer in a subject.

3. A method of treating cancer in a subject, comprising:
   (a) administering at least two formulations of tagged proteins to a subject in need of treatment, wherein the tagged proteins bind a cancer cell in the subject, and
   (b) administering at least two therapeutically-effective populations of AT-CAR-expressing effector cells to the subject, wherein the AT-CAR comprises a tag-binding domain, a transmembrane domain, and a T cell activation domain, where the T cell activation domain consists of one or more of the cytoplasmic region of OX40, the cytoplasmic region of HVEM, and FcRε, where the T cell activation domain does not comprise CD3ζ, and wherein the AT-CAR-expressing effector cells bind the tagged proteins and induce cancer cell death, thereby treating cancer in a subject.

4. The method of claim 1, wherein the tagged proteins are tagged with a tag selected from the group consisting of fluorescein isothiocyanate (FITC), streptavidin, biotin, dinitrophenol, peridinin chlorophyll protein complex, green fluorescent protein, phycoerythrin (PE), horse radish peroxidase, palmitoylation, nitrosylation, alkalanine phosphatase, glucose oxidase, and maltose binding protein.

5. The method of claim 1, wherein the protein of the tagged proteins is an antibody or an antigen-binding fragment thereof.

6. The method of claim 5, wherein the antibody or antigen-binding fragment thereof is cetuximab, nimotuzumab, panitumumab, retuximab, omalizumab, tositumomab, trastuzumab, gemtuzumab, or alemtuzumab, or an antigen-binding fragment of any one thereof.

7. The method of claim 1, wherein the tag-binding domain is an antibody or an antigen-binding fragment thereof.

8. The method of claim 1, wherein the tag-binding domain specifically binds FITC, biotin, PE, or streptavidin.

9. The method of claim 7, wherein the antigen-binding fragment is a single chain variable fragment (scFv).

10. The method of claim 7, wherein the antigen-binding fragment is a single chain variable fragment (scFv) that specifically binds FITC, biotin, PE, or streptavidin.

11. The method of claim 7, wherein the transmembrane domain is the hinge and transmembrane regions of the human CD8α chain.

12. The method of claim 1, wherein the effector cells of the population of AT-CAR-expressing effector cells comprises $CD3^+CD8^+$ T cells, $CD3^+CD4^+$ T cells, gamma delta T cells, cytokine induced killer (CIK) cells, natural killer (NK) cells, natural killer T (NKT) cells, tumor infiltrating lymphocytes (TILs), macrophages, or microglia.

13. The method of claim 1, wherein the formulation of tagged proteins is administered to the subject prior to administration of the therapeutically-effective population of AT-CAR-expressing effector cells.

14. The method of claim 1, wherein the formulation of tagged proteins are administered to the subject concurrently with administration of the therapeutically-effective population of AT-CAR-expressing effector cells.

15. The method of claim 1, wherein the formulation of tagged proteins are administered to the subject after administration of the therapeutically-effective population of AT-CAR-expressing effector cells.

16. The method of claim 1, wherein the formulation of tagged proteins and the therapeutically-effective population of AT-CAR-expressing effector cells are administered to the subject in any order.

17. The method of claim 1, wherein AT-CAR-expressing effector cell binding to the tagged proteins, which are bound to a cancer cell, induces cytolytic activation of the effector cells.

18. The method of claim 1, wherein the subject is a human.

* * * * *